United States Patent [19]
Wang et al.

[11] Patent Number: 5,637,765
[45] Date of Patent: Jun. 10, 1997

[54] PROCESS FOR THE PREPARATION OF FLUORINATED BENZOIC ACIDS

[75] Inventors: Xiu C. Wang, Park City, Ill.; Panos Kalaritis, New Providence, N.J.; Michelle L. Chang, Vernon Hills, Ill.

[73] Assignee: Abbott Laboratories, Abbott Park, Ill.

[21] Appl. No.: 462,235

[22] Filed: Jun. 5, 1995

Related U.S. Application Data

[60] Division of Ser. No. 232,117, May 2, 1994, abandoned, which is a continuation-in-part of Ser. No. 785,851, Oct. 31, 1991, abandoned.

[51] Int. Cl.$^6$ .................................................. C07C 205/00
[52] U.S. Cl. .............................. 562/438; 562/23; 560/83
[58] Field of Search ........................ 562/438, 23; 560/83

[56] References Cited

U.S. PATENT DOCUMENTS

| | | | |
|---|---|---|---|
| 4,160,032 | 7/1979 | Hardtman et al. | 424/274 |
| 4,239,901 | 12/1980 | Rainer | 560/34 |
| 4,730,000 | 3/1988 | Chu et al. | 514/254 |
| 5,543,144 | 8/1996 | Chang | 424/133.1 |

*Primary Examiner*—Marianne M. Cintins
*Assistant Examiner*—Keith MacMillan
*Attorney, Agent, or Firm*—Mona Anand; Thomas D. Brainard

[57] ABSTRACT

A process for the preparation of 2-chloro-4,5-difluorobenzoic acid and 2,4,5-trifluorobenzoic acid as well as synthetic intermediates useful in and prepared according thereto, comprising reacting a nitrobenzene having the formula

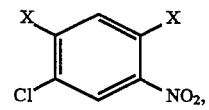

wherein X is chloro or fluoro, with an appropriate carbanion to form a compound having the formula

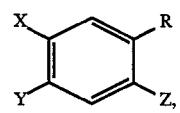

wherein one of Y and Z is chloro and the other is nitro, and R is a radical selected from the group consisting of —CCl$_3$, —CH$_2$NO$_2$, —CH(NO$_2$)R$^1$, —CH(CO$_2$R$^1$)$_2$, —CH(C(O)R$^2$)$_2$, —CH(CN)CO$_2$R$^1$, —CH(CO$_2$R$^1$)COR$^2$ and —COR$^2$ where R$^1$ is alkyl or arylalkyl and R$^2$ is alkyl, aryl or arylalkyl and, where appearing more than once in such a radical, R$^1$ and R$^2$ may be the same or different at each occurrence.

4 Claims, No Drawings

PROCESS FOR THE PREPARATION OF FLUORINATED BENZOIC ACIDS

This application is a division of U.S. patent application Ser. No. 08/232,117, filed May 2, 1994, now abandoned which is a continuation-in-part of U.S. patent application Ser. No. 07/785,851, filed Oct. 31, 1991, now abandoned.

TECHNICAL FIELD

The present invention relates to the preparation of starting materials for use in the synthesis of quinolone antibacterial agents. More particularly, the invention relates to a process for preparing certain halo-substituted benzoic acids and acetophenones which may be employed in quinolone syntheses, as well as novel compounds useful in such a process.

BACKGROUND OF THE INVENTION

Substituted 1,4-dihydro-4-oxoquinoline-3-carboxylic acid derivatives (hereinafter quinolones) are known to be effective antibacterial agents (see, for example, U.S. Pat. No. 4,730,000, issued Mar. 8, 1988 to Chu). Halo-substituted benzoic acids and their corresponding esters and acetophenones are useful as starting materials in the synthesis of such quinolones, as disclosed in the published European patent application of Kumai et al., No. 0 303 291, published Feb. 15, 1989.

In particular, 2-chloro-4,5-difluorobenzoic acid (CDFBA), 2,4,5-trifluorobenzoic acid (TFBA), and their respective analogous acetophenones are advantageous starting materials for quinolone synthesis. Known methods of preparing these compounds, however, suffer from a number of drawbacks, including complex chemistry requiring specialized equipment expensive or hard-to-obtain starting materials; materials hazards such as those associated with the use and decomposition of diazonium salts; and reactions having commercially undesirable selectivities and/or yields. There is therefore a continuing need for an improved process for preparing the above intermediates which overcomes some or all of these disadvantages.

SUMMARY OF THE INVENTION

Accordingly, a new process is disclosed for the preparation of CDFBA and TFBA from inexpensive and readily available starting materials. In one aspect of the present invention is disclosed a method for preparing a compound having the formula

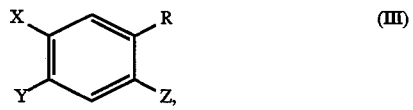

wherein X is chloro or fluoro; one of Y and Z is chloro and the other of Y and Z is nitro; and R is a radical selected from the group consisting of —CCl$_3$, —CH$_2$NO$_2$, —CH(NO$_2$)R$^1$, —CH(CO$_2$R$^1$)$_2$, —CH(C(O)R$^2$)$_2$, —CH(CN)CO$_2$R$^1$, —CH(CO$_2$R$^1$)COR$^2$ and —COR$^2$, where R$^1$ is alkyl or arylalkyl and R$^2$ is alkyl, aryl or arylalkyl and, where appearing more than once in such a radical, R$^1$ and R$^2$ may be the same or different at each occurrence. The method comprises reacting a nitrobenzene having the formula

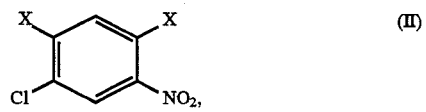

with an appropriate carbanion to form said compound (III). Such a carbanion may be generated by reacting a base with a nucleophile such as one selected from the group consisting of nitroalkanes, enamines, malonates, beta-ketoesters, cyanoacetates, malononitriles and beta-diketones. Bases which are suitable for this reaction i e, for example, those selected from the group consisting of amines, amidines, hydroxides, alkoxides, hydrides, carbonates and bicarbonates. A preferred embodiment of the method is one in which the base is 1,8-diazabicyclo [5.4.0]undec-7-ene (DBU) or 1,1,3,3-teuramethylguanidine, forming a substituted nitrobenzene product (III) in which R is —CH$_2$NO$_2$ or —CH(NO$_2$)CH$_3$, X is fluoro, Y is nitro, and Z is chloro.

In a second aspect of the present invention, a method is disclosed for preparing a compound having the formula

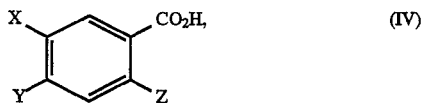

wherein X is chloro or fluoro; one of Y and Z is chloro; and the other of Y and Z is nitro. This method comprises reacting a substituted nitrobenzene, such as one having the formula

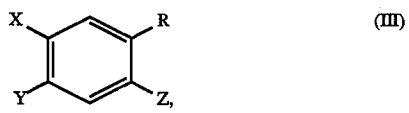

wherein R is selected from the group consisting of —CCl$_3$, —CH$_2$NO$_2$, —CH(NO$_2$)R$^1$, —CH(CO$_2$R$^1$)$_2$, —CH(C(O)R$^2$)$_2$, —CH(CN)CO$_2$R$^1$, —CH(CO$_2$R$^1$)COR$^2$ and —COR$^2$, where R$^1$ and R$^2$ are as previously defined, with an appropriate acid. In a preferred embodiment, R is —CH(CO$_2$R$^1$)$_2$ or —CH(NO$_2$)R$^1$ and the acid is sulfuric or nitric, with about 50% sulfuric or about 40% nitric acid being most preferred. The product (IV) of this oxidation reaction may then be recrystallized, as for example from ethyl acetate or methylene chloride.

In a further aspect of the present invention, a method is disclosed for preparing a compound having the formula

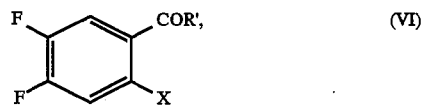

wherein X is chloro or fluoro and R' is hydroxy or fluoro. The method comprises reacting a benzoyl chloride having the formula

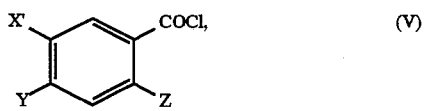

wherein X' is chloro or fluoro, one of Y and Z is chloro, and the other of Y and Z is nitro, with an appropriate fluoride, and preferably with lithium, sodium, potassium, cesium or alkylammonium fluoride. This reaction is subject to the proviso that when X in formula (VI) is chloro, Z in formula (V) must also be chloro.

In a preferred embodiment of the above method, Y is nitro; Z is chloro; the fluoride used is potassium fluoride; and the fluorination reaction is carried out in N,N-dimethylformamide (DMF) at atmospheric refluxing temperature. In all cases, however, a product of fluorination may be hydrolyzed to obtain a compound of formula (VI) where R' is hydroxy. Alternatively, the fluorination product may be distilled to obtain a compound of formula (VI) where R' is fluoro.

Also comprised by the present invention are novel synthetic intermediates which may be prepared according to the above inventive methods. Included are compounds having the formula

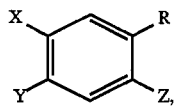
(III)

wherein, as before, X is chloro or fluoro; one of Y and Z is chloro and the other is nitro; and R is selected from the group consisting of —CCl$_3$, —CH$_2$NO$_2$, —CH(NO$_2$)R$^1$, —CH(CO$_2$R$^1$)$_2$, —CH(C(O)R$^2$)$_2$, —CH(CN)CO$_2$R$^1$, —CH(CO$_2$R$^1$)COR$^2$ and —COR$^2$, where R$^1$ and R$^2$ are as previously defined. Other compounds of the invention are those which have the formula

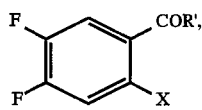
(VI)

wherein X again is chloro or fluoro, and R' is hydroxy or chloro.

DETAILED DESCRIPTION OF THE INVENTION

The methods and compounds of the present invention are herein described using certain terms which, except where otherwise indicated, are accorded the following definitions:

The term "alkoxide" refers to a compound of the formula R$^3$OM or (R$^3$O)$_2$M, where R$^3$ is alkyl as defined below and M is a suitable cation such as lithium, sodium, potassium or magnesium.

The term "alkyl" refers to a straight- or branched-chain, saturated hydrocarbon radical of one to ten carbon atoms including, but not limited to, methyl, ethyl, propyl, isopropyl, n-butyl, sec-butyl, tert-butyl and the like.

The term "amidine" refers to a compound of the formula R$^4$C(NR$^5$R$^6$)=NR$^7$ where R$^5$, R$^6$ and R$^7$ are independently alkyl and R$^4$ is selected from amino and alkyl, or where either or both of R$^5$ and R$^6$ taken together with either or both of R$^4$ and R$^7$ form a group having the formula —(CH$_2$)$_m$— where m is two to six including, but not limited to, DBU, 1,5-diazabicyclo [4.3.0]non-5-ene (DBN), guanidines such as 1,1,3,3-tetramethyl-guanidine or 2-t-butyl-1,1,3,3-tetramethylguanidine and the like.

The term "amine" refers to a tertiary amine of the formula N(R$^8$)$_3$ or a tertiary diime of the formula N(R$^9$)$_3$N, where R$^8$ is alkyl of from two to ten carbons or arylalkyl having an alkyl component of from two to ten carbons and R$^9$ is a group of the formula —(CH$^2$)$_n$— where n is two to four, including, but not limited to, triethylamine, triethylenediamine and the like.

The term "aryl" refers to a cyclic or fused bicyclic, aromatic hydrocarbon radical such as phenyl or naphthyl.

The term "arylalkyl" refers to an aryl radical linked to the parent molecule via an alkyl group including, but not limited to, benzyl, phenylethyl, phenylbutyl, naphthylmethyl, naphthylpentyl and the like.

The term "beta-diketone" refers to a compound of the formula R$^{11}$C(O)CH(R$^{10}$)C(O)R$^{12}$, where R$^{10}$ is selected from hydrogen, alkyl, aryl and arylalkyl and R$^{11}$ and R$^{12}$ are independently alkyl, aryl or arylalkyl.

The term "beta-ketoester" refers to a compound of the formula R$^{11}$C(O)CH(R$^{13}$)CO$_2$R$^8$, where R$^{13}$ is selected from hydrogen, alkyl and arylalkyl, R$^{11}$ is alkyl, aryl or arylalkyl, and R$^8$ is alkyl or arylalkyl.

The term "bicarbonate" refers to a compound of the formula M$^1$HCO$_3$, where M$^1$ is a suitable cation such as lithium, sodium or potassium.

The term "carbonate" refers to a compound of the formula (M$^1$)$_2$CO$_3$ where M$^1$ is a suitable monovalent cation such as lithium, sodium or potassium, or of the formula M$^2$CO$_3$ where M$^2$ is a divalent cation such as magnesium or calcium.

The term "cyanoacetate" refers to a compound of the formula CH(CN)(R$^{14}$)CO$_2$R$^{15}$, where R$^{14}$ and R$^{15}$ are independently selected from hydrogen, alkyl and arylalkyl.

The term "enamine" refers to a compound of the formula C(NR$^{16}$R$^{17}$)(R$^{14}$)=CHR$^{15}$, where R$^{16}$ and R$^{17}$ are independently alkyl of one to ten carbons and R$^{14}$ and R$^{15}$ are independently selected from hydrogen, alkyl and arylalkyl.

The term "fluoride" refers to a compound of the formula M$^3$F, where M$^3$ is a suitable cation such as lithium, sodium, potassium, cesium or alkylammonium.

The term "hydride" refers to a compound of the formula M$^1$H, where M$^1$ is a suitable cation such as lithium, sodium or potassium.

The term "hydroxide" refers to a compound of the formula M$^4$OH, where M$^4$ is a suitable cation such as lithium, sodium, potassium, magnesium or alkylammonium.

The term "malonate" refers to a compound of the formula CH(R$^{13}$)(CO$_2$R$^{18}$)$_2$, where R$^{13}$ and R$^{18}$ are selected from hydrogen, alkyl and arylalkyl.

The term "malononitrile" refers to a compound of the formula CH(R$^{10}$)(CN)$_2$, where R$^{10}$ is selected from hydrogen, alkyl, aryl and arylalkyl.

The term "nitroalkane" refers to a compound having the formula CH(R$^{19}$)(R$^{20}$)NO$_2$, where R$^{19}$ and R$^{20}$ are independently selected from hydrogen, alkyl and aryl.

SCHEME I

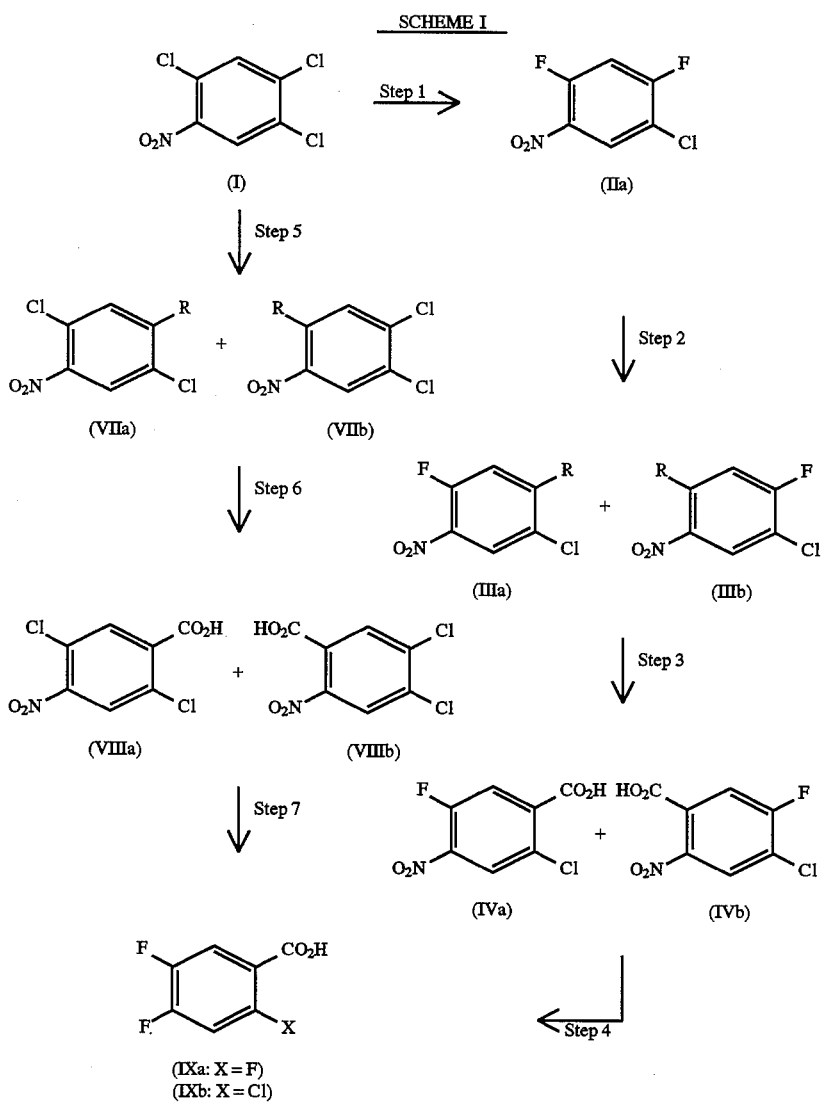

(IXa: X = F)
(IXb: X = Cl)

The present invention will be better understood in connection with the preceding reaction scheme. In Scheme I, 2,4,5-trichloronitrobenzene (I) is converted to 5-chloro-2,4-difluoronitrobenzene (IIa) in a fluorination reaction (reaction step 1) using a fluorinating reagent such as potassium fluoride. Upon exposure to an action of a nucleophile such as nitromethane or malonate, compound (IIa) undergoes a nucleophilic substitution reaction (step 2) to produce isomeric nitrobenzene derivatives (IIIa) and (IIIb), which are then oxidized (in step 3) to the corresponding benzoic acids (IVa) and (IVb) using, for example, nitric acid. Subsequent fluorodenitration, fluorodechlorination and hydrolysis (in step 4) of the mixture of benzoic acids (IVa) and (IVb) results in the formation of the quinolone synthesis starting material TFBA (IXa, where X is fluoro), while fluorodenitration alone and hydrolysis of the isolated benzoic acid (IVa) yields the starting material CDFBA (IXb, where X is chloro). Isolation of a particular isomer from a product mixture may be accomplished by known separatory techniques, such as crystallization or column chromatography.

Alternatively, 2,4,5-trichloronitrobenzene (I) may without prior fluorination undergo nucleophilic substitution (in reaction step 5) to form isomeric dichloronitrobenzene derivatives (VIIa) and (VIIeb), followed by oxidization (in step 6) to the corresponding benzoic acids (VIIIa) and (VIIIb). The mixture of benzoic acids (VIIIa) and (VIIIb) is then fluorodenitrated, fluorodechlorinated and hydrolyzed (in step 7) to form TFBA (IXa).

Not shown but obtainable via Scheme I are the quinolone starting materials 2-chloro-5-fluoro-4-nitroacetophenone and 4-chloro-5-fluoro-2-nitroacetophenone, which can be prepared from nitrobenzene derivatives (IIIa) and (IIIb) via a Nef reaction. Also omitted from the scheme, but included among the compounds of the present invention, are benzoyl halide intermediates (V) and (VI) which are produced during reaction steps 4 and 7 and discussed in greater detail below.

The above procedures may be carried out using a variety of reagents and reaction conditions. In the substitution reactions of steps 2 and 5, which are analogous and are demonstrated in Examples 2, 7–10 and 14–18 below, a variety of solvents are suitable including common protic or aprotic polar solvents such as DMF, dimethyl sulfoxide (DMSO), dioxane, pyridine, THF, N,N-dimethylacetamide (DMAC), and two- to five-carbon alcohols, as well as mixtures thereof such as DMSO/water. Alternatively, the nucleophilic substitutions of these steps may be performed neat in the presence of a phase-transfer catalyst, as for example tris(3,6-dioxaheptyl)amine (TDA), tricaprylylmethylammonium chloride, tetrabutylammonium fluoride (TBAF) or tetrabutylammonium chloride (TBAC).

The oxidation reactions of steps 3 and 6 may be carried out as single- or two-step reactions, as demonstrated in Examples 3, 5, 11 and 12, and are likewise capable of considerable variation. When performed stepwise, the oxidation may be performed neat or in a solvent such as water, acetic acid or a water-miscible organic solvent, as for example dioxane. Reagents such as acetic acid/HCl, DMSO/NaCl or $H_2SO_4$ may be used, optionally followed by, for example, nitric acid, permanganate or potassium peroxymonosulfate, with the reaction proceeding at from about 25° C. to about 110° C. Alternatively, when run as a one-step reaction the reaction may be carded out neat or in water, using nitric acid alone or permanganate in acid at from about 25° C. to about 110° C.

The fluorodenitration and/or fluorodechlorination reactions of steps 4 and 7 are demonstrated in Examples 4, 6 and 13. These may be performed over a temperature range of about 80° C. to about 250° C., depending on the presence or absence of a phase-transfer catalyst such as tetraphenylphosphonium bromide (TPPB), TBAF or TBAC. Polar or nonpolar, aprotic solvents such as DMF, 1-methyl-2-pyrrolidinone (NMP), DMAC, 1,3-dimethyl-2-imidazolidinone (DMI), tetramethylene sulfone ($TMSO_2$), toluene and xylenes are preferred, and may be used either alone or in combination. The fluorinations of steps 4 and 7 are preceded by the formation, using thionyl chloride, of benzoyl chloride intermediates (V); if desired, these compounds may be isolated without further reaction.

Reagents and conditions may be chosen in each of the above reactions to select for a particular isomer or product. In a preferred embodiment of the oxidation reaction, for example, a product is obtained in which the major component, 4-nitrobenzoic acid, is present in a 23:1 ratio to the 2-nitrobenzoic acid isomer, using a mixture of alpha-aryl nitroalkanes (IIIa and IIIb, where R is —$CH(NO_2)R^1$) in which the ratio of the corresponding isomers is only 2:1 (Example 5) as a starting material. Likewise, the fluorination of benzoyl chloride intermediates (V) may be carried out under conditions which favor (i) fluorinating at all positions to form a trifluorobenzoyl fluoride intermediate (Example 4); (ii) forming a chlorodifluorobenzoyl fluoride intermediate without replacement of the ring chlorine (Example 6); or (iii) selectively converting a mixture of benzoic acids (IVa and IVb, in a ratio of about 2.5:1) to a single isomer, 2-chloro-4,5-difluorobenzoyl fluoride, again without replacing the ring chlorine (Example 13).

The foregoing methods and compounds of the present invention may be better understood by reference to the following Examples, which are provided for illustration and are not intended as a limitation upon the present invention.

EXAMPLE 1

5-Chloro-2,4-difluoronitrobenzene (2)

200 g (0.883 mol) of 2,4,5-trichloronitrobenzene and 128.4 g (2.21 mol) of KF in 500 ml of tetramethylenesulfone were reacted at 200° C. under nitrogen for 3.5 hours. To the mixture was added 500 ml of ethyl acetate and the precipitate was filtered. The filtrate was washed with brine, dried over magnesium sulfate and concentrated. Distillation at 85°–90° C./0.9 mm afforded pure compound 2 with more than 70% yield.

$^1$H-NMR from $CDCl_3$ ($\delta$ ppm): 7.17(dd, 1H, J=8 Hz, 9 Hz), 8.26 (dd, 1H, J=7.5 Hz, 7.5 Hz).

MS(m/z): 193 ($M^+$).

EXAMPLE 2

5-Chloro-2-fluoro-4-(nitromethyl)nitrobenzene (3) and 5-Chloro-4-fluoro-2-(nitromethyl)nitrobenzene (4)

DBU (16.5 g, 0.11 mol) in 20 ml of ethyl acetate was cooled in an ice-bath and treated with nitromethane (3.1 ml, 0.057 mol). The solution was stirred under nitrogen for 10 min and 10.0 g of compound 2 (0.052 mol, from example 1) in 20 ml of ethyl acetate was added dropwise at the same temperature. The dark red mixture was stirred for 2 hours and then warmed up to room temperature. The mixture was treated with 10% HCl (10 ml) and extracted with ethyl acetate. The ethyl acetate layer was washed with brine, dried over sodium surf ate, filtered, and concentrated under reduced pressure to give the product (10.9 g, 89.9%). The product consisted of compounds 3 and 4 in a ratio of 2:1 based on NMR analysis. The two isomers were separated by column chromatography (silica gel, 10% ethyl acetate/hexanes).

Compound 3: yellowish crystals, mp 70°–72° C. $^1$H-NMR from $CDCl_3$ ($\delta$ ppm): 5.64 (s, 2H), 7.47 (d, 1H, J=10.5 Hz), 8.22 (d, 1H, J=7 Hz).

Compound 4: $^1$H-NMR from $CDCl_3$ ($\delta$ ppm): 5.81 (s, 2H), 7.31 (d, 1H, J=9 Hz), 8.44 (d, 1H, J=6 Hz).

MS (m/z): 234 ($M^+$).

EXAMPLE 3

2-Chloro-5fluoro-4-nitrobenzoic and (5) and 4-Chloro-5-fluoro-2-nitrobenzoic acid (6)

The product from Example 2 (12.1 g, 0.052 mol) in of 25 ml of conc. nitric acid and 20 ml of water was heated at 90° C. for 2 hours. The solution was cooled to room pemperature and diluted with 20 ml of water. The mixture was extacted with ethyl acetate. The ethyl acetate solution was washed with brine and extracted with saturated aqueous sodium bicarbonate. The water layer was separated, acidified with conc. HCl, and extracted with ethyl acetate. The organic layer was dried over sodium sulfate and concentrated. The residue was recrystallized from ethyl acetate to afford 7.5 g (66%) of the product which consisted of compounds 5 and 6 in a ratio of 2:1 based on NMR analysis. The two isomers were separated by crystallization from ethyl acetate-methylene chloride.

Compound 5: mp 129°–131° C. (EtOAc-$CH_2Cl_2$). $^1$H-NMR from DMSO-$d_6$ ($\delta$ ppm): 8.01 (d, 1H, J=11 Hz), 8.36 (d, 1H, J=7 Hz), 14.2 (br, 1H).

Compound 6: $^1$H-NMR from DMSO-$d_6$ ($\delta$ ppm): 7.96 (d, 1H, J=9 Hz), 8.45 (d, 1H, J=6 Hz), 14.2 (br, 1H).

MS (m/z): 219 ($M^+$).

EXAMPLE 4

2,4,5-Trifluorobenzoic acid (7)

A mixture of compounds 5 and 6 from Example 3 (10.95 g, 0.05 mol) was treated with thionyl chloride (5.47 ml, 0.075 mol) and the mixture was refluxed under nitrogen for 4 hours. The excess of thionyl chloride was removed by distillation and the remainder distilled at 85°–90° C./0.7 mm to afford 10.6 g (89.5%) of the corresponding benzoyl chlorides.

The benzoyl chlorides (10 g, 42 mmol) were dissolved in 30 ml of tetramethylenesulfone. To this was added 15 g (26 mmol) of spray-dried KF and 17.5 g of phthalloyl dichloride. The mixture was heated at 165° C. for 3 hours under nitrogen. The product 2,4,5trifluorobenzoyl fluoride was distilled at 65°–70° C./25 mm. Water was added to the distillate and the benzoic acid 7 was collected by filtration as white crystals (65% yield).

$^1$H-NMR from CDCl$_3$-CD$_3$OD (δ ppm): 7.04 (m, 1H), 7.82 (m, 1H).

MS (m/z): 176 (M$^+$).

EXAMPLE 5

Selective Formation of 2-Chloro-5-fluoro-4-nitrobenzoic acid (5)

The product prepared in Example 2 (2 g, 2.0 retool) in 3 ml of conc. sulfuric acid and 2 ml of water was heated at 100° C. for 40 min. The mixture was cooled, diluted with 4 ml of water, and extacted with ethyl acetate. The ethyl acetate layer was partitioned with saturated sodium bicarbonate (5 ml×3). The aqueous layer was acidified and extracted with ethyl acetate. The combined ethyl acetate fractions were dried over magnesium sulfate, and concentrated. The residue was recrystallized from ethyl acetate to form a crystalline product (0.31 g, 50%) consisting of compounds 5 and 6 in a ratio of 23:1 based on NMR data.

EXAMPLE 6

2-Chloro-4,5-difluorobenzoic acid (8)

The product of Example 5 (20 g, 91 mmol) was suspended in 60 ml of thionyl chloride and heated to reflux for 3 hours under nitrogen. The excess of thionyl chloride was distilled off and the resultant acid chloride was dissolved in 40 ml of tetramethylenesulfone. To the solution was added 16 g (276 mmol) of spray-dried KF and 38.5 g of 4-chlorosulfonyl chloride. (This Example was also duplicated with 40 g benzenesulfonyl chloride in place of the 4-chlorosulfonyl chloride, with substantially identical results.) The mixture was then heated at 125° C. for 3 hours under nitrogen. Distillation of the reaction mixture at 70°–75° C./15 mm afforded pure 2-chloro-4,5-difluorobenzoyl fluoride. The liquid product was hydrolyzed with water and dried under vacuum to give 75% yield of compound 8 as white crystals.

$^1$H-NMR from DMSO-d$_6$ (δ ppm): 7.82 (dd, 1H, J=11 Hz, 7 Hz), 7.91 (dd, 1H, J=11 Hz, 9 Hz).

MS (m/z): 192 (M$^+$).

EXAMPLE 7

Dimethyl 2-(2-chloro-5-fluoro-4-nitrophenyl) malonate (9) and Dimethyl 2-(4-chloro-5-fluoro 2-nitrophenyl)malonate (10)

Diethyl 2-(2-chloro-5-fluoro-4-nitrophenyl)malonate (9a) and Diethyl 2-(4-chloro-5-fluoro-2-nitrophenyl) malonate (10a)

Variation 1: The preparations of compounds 9 and 9a and their respective isomers 10 and 10a were carried out in the same manner as in Example 2 using dimethyl and diethyl malonate, respectively, in place of nitromethane. The products were isolated in quantitative yield. In each reaction, a 1.2:1 ratio mixture of the 2-chloro-5-fluoro 4-nitrophenyl and 4-chloro-5-fluoro-2-nitrophenyl malonates was formed, based on NMR analysis. The isomeric products were separated by column chromatography (silica gel, 10% EtOAc/hexanes).

Variation 2: To suspensions of lithium hydroxide monohydrate (47.9 g, 1.14 mol) in DMSO (100ml) at 15° C. were added the appropriate dialkyl malonate (86.4 ml, 0.57 mol). The mixtures were stirred for 15 min under nitrogen, and a solution of compound 2 (from Example 1, 100 g, 0.52 mol) in 50 ml of DMSO added dropwise. The dark red mixtures were stirred under nitrogen at room temperature for 3 hours, quenched with 10% HCl, and extracted with ethyl acetate. The ethyl acetate layers were washed with brine and dried over magnesium sulfate. The solvent was removed under reduced pressure to give the pure products (quantitative yield), consisting in each case of the 2-chloro-5-fluoro-4-nitrophenyl and 4-chloro-5-fluoro-2-nitrophenyl malonates in a ratio of 1.2:1 based on NMR analysis.

Compound 9: mp 51°–51° C. $^1$H-NMR from CDCl$_3$ (δ ppm): 3.82 (s, 6H), 5.26 (s, 1H), 7.59 (d, 1H, J=10 Hz), 8.15 (d, 1H, J=7 Hz).

Compound 10: $^1$H-NMR from CDCl$_3$ (δ ppm): 3.82 (s,6H), 5.37 (s, 1H), 7.48 (d, 1H, J=10 Hz), 8.22 (d, 1H, J=7 Hz).

MS (m/z): 323 ([M+NH$_4$]$^+$).

Compound 9a: $^1$H-NMR from CDCl$_3$ (δ ppm): 1.30 (t, 6H, J=7 Hz), 4.29 (q, 4H), 5.22 (s, 1H), 7.60 (d, 1H, J=11 Hz), 8.15 (d, 11H, J=7 Hz).

Compound 10a: $^1$H-NMR from CDCl$_3$ (δ ppm): 1.31 (t, 6H, J=7 Hz), 4.29 (q, 4H), 5.32 (s, 1H), 7.40 (d, 1H, J=9 Hz), 8.22 (d, 1H, J=7 Hz).

MS (m/z): 351 ([M+NH$_4$]$^+$).

EXAMPLE 8

Methyl 2-(2-chloro-5-fluoro-4-nitrophenyl) cyanoacetate (11) and Methyl 2-(4-chloro-5-fluoro-2-nitrophenyl)cyanoacetate (12)

The preparation of compounds 11 and 12 was carried out in a manner analogous to that of Example 2 using 1 g (5.2 retool) of compound 2 (from Example 1) and methyl cyanoacetate. The product consisted of 11 and 12 in a ratio of 1:2 with a total yield of 100%. The two isomers were separated by column chromatography (silica gel, 10% EtOAc/hexanes).

Compound 11: $^1$H-NMR from CDCl$_3$(δ ppm): 3.90 (s, 3H), 5.21 (s, 1H), 7.62 (d, 1H, J=11 Hz), 8.20 (d, 1H, J=7 Hz).

Compound 12: off-white solid, mp 92.5°–94° C. $^1$H-NMR from CDCl$_3$ (δ ppm): 3.90 (s, 3H), 5.70 (s, 1H), 7.61 (d, 1H, J=9 Hz), 8.39 (d, 1H, J=7 Hz).

MS (m/z): 290 ([M+NH$_4$]$^+$).

EXAMPLE 9

Ethyl 2-(2-Chloro-5-fluoro-4-nitrophenyl) acetoacetate (13) and Ethyl 2-(4-chloro-5-fluoro-2-nitrophenyl)acetoacetate (14)

The preparation of compounds 13 and 14 was conducted in the same manner as in Example 7 with 0.5 g of compound 2 (from Example 1) and ethyl acetoacetate. The product consisted of compounds 13 and 14 in a ratio of 1:1 with a total yield of 0.7 g (89%). The two isomeric products were separated by column chromatography (silica gel, 10% EtOAc/hexanes).

Compound 13: $^1$H-NMR from CDCl$_3$ (δ ppm): 1.20 (t, 3H, J=7.5 Hz, 7.5 Hz), 1.84 (s, 3H), 4.24 (q, 2H), 7.29 (d, 1H, J=11 Hz), 8.16 (d, 1H, J=7 Hz), 13.15 (s,1H).

Compound 14: $^1$H-NMR from CDCl$_3$ (δ ppm): 1.12 (t, 3H, J=7 Hz), 1.90 (s, 3H), 4.16 (q, 2H), 7.09(d, 1H, J=8 Hz), 8.16 (d, 1H, J=7 Hz), 13.04 (s, 1H).

MS (m/z): 321 ([M+NH$_4$]+).

EXAMPLE 10

5-Chloro-2-fluoro-4-(trichloromethyl)nitrobenzene (15) and 5-Chloro-4-fluoro-2-(trichloromethyl) nitrobenzene 16

The preparation of compounds 15 and 16 was carded out as in Example 2 using chloroform and compound 2. The product consisted of compounds 15 and 16 in a ratio of 1:1 with a total yield of 44%.

Compound 15: $^1$H-NMR from CDCl$_3$ (δ ppm): 6.91 (d, 1H, J=12 Hz), 8.12 (d, 1H, J=7 Hz).

Compound 16: $^1$H-NMR from CDCl$_3$ (δ ppm): 6.32 (d, 1H, J=13 Hz), 8.29 (d, 1H, J=7 Hz).

EXAMPLE 11

2-Chloro-5-fluoro-4-nitrobenzoic acid (5) and 4-Chloro-5-fluoro-2-nitrobenzoic acid (6) From Oxidation of Dialkyl (Chloro-fluoro-nitrophenyl) malonates Variation 1: Each of the mixtures of dialkyl malonate compounds 9/10 and 9a/10a prepared in Example 7 (2 g, 6.56 mmol) and 13 ml of 40% HNO$_3$ were heated at 70° C. for 3 hours and then at 90° C. for 13.5 hours. The reaction mixtures were cooled to room temperature and the precipitates filtered. The solid products collected were washed with water, dissolved in ethyl acetate, and extracted with saturated aqueous sodium bicarbonate. The aqueous layers were acidified to pH 2 with conc. HCl and extracted with ethyl acetate. The organic layers were dried over magnesium sulfate and concentrated to give light-yellow crystalline product (0.72 g, 50%). The $^1$H-NMR spectra of the products showed them to be mixtures of compounds 5 and 6 in a 2.6: ratio.

Variation 2: A mixture of the dimethyl malonates 9 and 10 from Example 7 (20 g, 0.06 mol) and 60 ml of 25% of sulfuric acid was heated at refluxing temperature for 21 hours. The solution was cooled in an ice bath and the precipitate collected by filtration. The solid material was treated with 60 ml of 40% of nitric acid and the mixture refluxed for 30 hours. The precipitate formed upon cooling of the solution was filtered, washed with water, and dried in vacuum. More product was obtained by extracting the mother liquor with ethyl acetate. The product (total yield 8.81 g, 67%) consisted of compounds 5 and 6 in a ratio of about 4:1, based on NMR spectrum analysis. Crystallization of the product from variation 1 or variation 2 from ethylacetate gave pure compound 5.

EXAMPLE 12

2-Chloro-5-fluoro-4-nitrobenzoic acid (5) and 4-Chloro-5-fluoro-2-nitrobenzoic acid (6) From Oxidation of Ethyl (Chloro-fluoro-nitrophenyl) acetoacetates The oxidation of the acetoacetates 13 and 14 from Example 9 was conducted in the same manner as is described in Example 11. The product obtained (0.72 g, 50%) consisted of compounds 5 and 6 in a 1:1 ratio based on NMR analysis.

EXAMPLE 13

2-Chloro-4,5-difluorobenzoic acid (8) via Selective Fluorination

The combined benzoic acids made in each of Examples 3, 11 and 12 (consisting of compounds 5 and 6 in a ratio of about 2:1) were converted to the corresponding acid chlorides as in Example 4. The acid chlorides (2 g, 8.4 mmol) were dissolved in 4 ml of tetramethylenesulfone and treated with spray-dried KF (2.0 g, 34.5 mmol). The mixture was heated at 150° C. under nitrogen for 3 hours and the product distilled at 70°–75° C./15 mm. The acid fluoride collected was hydrolyzed with water and the product was dried in vacuum to give pure compound 8 as the only product (0.4 g, 24%).

EXAMPLE 14

2,5-Dichloro-4-(1-nitroethyl)nitrobenzene (17) and 4,5-Dichloro-2-(1-nitroethyl)nitrobenzene (18)

To a solution of 75.5 g of DBU (0.486 mol) in 350 ml of ethyl acetate cooled in an ice bath were sequentially added dropwise 18.2 g (0.243 mol) of nitroethane and 50 g (0.221 mol) of 2,4,5-trichloronitrobenzene (compound 1) in 100 ml of ethyl acetate. The resultant mixture was stirred under nitrogen at room temperature for 2 days. The mixture was acidified with 10% HCl and extracted with ethyl acetate. The ethyl acetate solution was washed with brine, dried over magnesium sulfate, and concentrated. The product obtained consisted of compounds 17 and 18 in a ratio of 1:3 based on NMR analysis (50.3 g, 86%). The two isomers were separated by chromatography (silica gel, 10% EtOAc/hexanes).

2,5-Dichloro-4-(1-nitroethyl)nitrobenzene (17): $^1$H-NMR from CDCl$_3$ (δ ppm): 1.97 (d, 3H, J=7 Hz), 6.06 (s, 1H), 7.67 (s, 1H), 8.01(s, 1H).

4,5-Dichloro-2-(1-nitroethyl)nitrobenzene (18): mp 48°–49° C. $^1$H-NMR from CDCl$_3$ (δ ppm): 2.01(d, 3H, J=7 Hz), 6.25 (q, 1H), 7.71(s, 1H), 8.23 (s, 1H).

MS(m/z): 282([M+NH$_4$]$^+$).

EXAMPLE 15

Dimethyl 2-(4,5-dichloro-2-nitrophenyl)malonate (19) and Dimethyl 2-(2,5-dichloro-4-nitrophenyl) malonate The preparation of compounds 19 and 20 was carried out as in Example 2 using dimethyl malonate in place of nitromethane. The yellowish crystalline product consisted of compounds 19 and 20 in a ratio of 2.5:1 with a total yield of 100%.

Compound 19: $^1$H-NMR from CDCl$_3$ (δ ppm): 3.76 (s, 6H), 5.24 (s, 1H), 7.78 (s, 1H), 7.97 (s, 1H).

Compound 20: $^1$H-NMR from CDCl$_3$ (δ ppm): 3.83 (s, 6H), 5.31 (s, 1H), 7.65 (s, 1H), 8.21 (s, 12H).

MS (m/z): 339 ([M+NH$_4$]$^+$).

EXAMPLE 16

Methyl 2-(2,5-Dichloro-4-nitrophenol)cyanoacetate (21) and Methyl 2-(4,5-Dichloro-2-nitrophenyl) cyanoacetate (22)

The preparation of compounds 21 and 22 was carried out as in Example 2 using methyl cyanoacetate in place of nitromethane. The product consisted of compounds 21 and 22 in a ratio of 1:3 with a total yield of 93%. The two isomers were separated by column chromatography (silica gel, 8% EtOAc/hexanes).

Compound 21: $^1$H-NMR from CDCl$_3$ (δ ppm): 3.90 (s, 3H), 5.20 (s, 1H), 7.82 (s, 1H), 8.01 (s, 1H).

Compound 22: white solid, mp 98.7°–99.8° C. $^1$H-NMR from CDCl$_3$ (δ ppm): 3.90 (s, 3H), 5.68 (s, 1H), 7.89 (s, 1H), 8.48 (s, 1H).

MS (m/z): 306 ([M+NH$_4$]$^+$).

EXAMPLE 17

Ethyl 2-(2,5-Dichloro-4-nitrophenyl)acetoacetate (23) and Ethyl 2-(4,5-Dichloro-2-nitrophenyl) acetoacetate (24)

The preparation of compounds 23 and 24 was carried out as in Example 7 using ethyl acetoacetate in place of nitromethane. The product consisted of compounds 23 and 24 in a ratio of 1:3 with a total yield of 90%. The two isomers were separated by column chromatography (silica gel, 8% ethyl acetate/hexanes).

Compound 23: $^1$H-NMR from CDCl$_3$ (δ ppm): 1.20 (t, 3H, J=7.5 Hz), 1.85 (s, 3H), 4.24 (m, 2H), 7.42 (s, 1H), 8.0 (s, 1H), 13.15 (s, 1H).

Compound 24: $^1$H-NMR from CDCl$_3$ (δ ppm): 1.13 (t, 3H, J=7.5 Hz), 1.91 (s, 3H), 4.22 (m, 2H), 7.40 (s, 1H), 8.14 (s, 1H), 13.05 (s, 1H).

MS if/z): 337 ([M+NH$_4$]$^+$)

EXAMPLE 18

4,5-Dichloro-2-nitrobenzoic acid (25) and 2,5-Dichloro-4-nitrobenzoic acid (26)

A mixture of 308 g (0.881 mol) of the malonates from Example 15, 150 ml of HOAc, 50 ml of water, and 150 ml of conc. HCl was heated at reflux for 2 days and then cooled to room temperature. The precipitate was collected by filtration, washed with water, treated with 200 ml of conc. HNO$_3$ and the mixture refluxed for 2 days. The solution was cooled to room temperature and the light yellow precipitate was filtered, washed with water, and dried in vacuum. The benzoic acids obtained consisted of compounds 25 and 26 in a ratio of 1.8:1 (total yield: 170 g, 82%).

Compound 25: $^1$H-NMR from DMSO-d$_6$ (δ ppm): 8.02 (S, 1H), 8.17 (S, 1H). Compound 26: $^1$H-NMR from DMSO-d$_6$ (δ ppm): 8.09 (s, 1H), 8.15 (s, 1H).

EXAMPLE 19

2,4,5-Trifluorobenzoic acid (7)

The benzoic acids from Example 18 were converted to the corresponding acid chlorides as in Example 4 with thionyl chloride. The acid chlorides were then reacted with KF in TMSO$_2$ as described in Example 4 to produce 2,4,5-triflurobenzoic acid (after hydrolysis of the trifluorobenzoyl fluoride) in a 15% yield.

EXAMPLE 20

2-Chloro-5-fluoro-4-(1-nitroethyl)nitrobenzene (27) and 4-Chloro-5-fluoro-2-(1-nitroethyl)nitrobenzene (28)

A solution of 1.4 ml (10.2 mmol) of DBU in 2 ml of ethyl acetate was cooled to 0° C. and treated sequentially with 0.38 ml (5.3 mmol) of nitroethane and 1.0 g (5.2 mmol) of compound 2 in 3 ml of ethyl acetate. The dark-red solution was stirred for 1 hour (0° C–20° C.) and then acidified with 10% HCl. The mixture was extracted with ethyl acetate, and the ethyl acetate solution dried over sodium sulfate and concentrated to give 1.1 g (84%) of pure compounds 27 and 28 in a ratio of 2:1. The two isomeric products were separated by column chromatography (silica gel, 10% EtOAc/hexanes).

Compound 27: $^1$H-NMR from CDCl$_3$ (δ ppm): 1.96 (d, 3H, J=7 Hz), 6.08 (q, 1H), 7.46 (d, 1H, J=1 1 Hz), 8.20 (d, 1H, J=6.5 Hz).

Compound 28: $^1$H-NMR from CDCl$_3$ (δ ppm): 2.0 (d, 3H, J=7 Hz), 6.28 (q, 1H), 7.42 (d, 1H, J=10 Hz), 8.25 (d, 1H, J=6.5 Hz).

MS (m/z): 248 (M$^+$).

EXAMPLE 21

2-Chloro-5-fluoro-4-nitroacetophenone (29) and 4-Chloro-5-fluoro-2-nitro-acetophenone (30)

The product from Example 18 (1.0 g, 4.0 mmol) was dissolved in 5 ml of methanol and cooled to 0° C. To the solution were sequentially added 10 ml of 30% H$_2$O$_2$ and 4.0 g (29 mmol) of potassium carbonate in 10 ml of water. The mixture was stirred overnight at room temperature and partitioned with ethyl acetate. The ethyl acetate layer was washed with 5% HCl and then brine, and was dried with sodium sulfate. The solvent was evaporated to give 85.7% of the product which consisted of compounds 29 and 30 in a ratio of 2:1. The two isomers were separated by columnchromatography (silica gel, 8% ethyl acetate-hexanes).

Compound 29: mp 105.4°–106.7° C. $^1$H-NMR from CDCl$_3$ (δ ppm): 2.69 (s, 3H), 7.46 (d, 1H, J=10 Hz), 8.15 (d, 1H, J=6 Hz).

Compound 30: mp 117.7°–119.7° C. $^1$H-NMR from CDCl$_3$ (δ ppm): 2.55 (s, 3H), 7.23 (d, 1H, J=11 Hz), 8.25 (d, 1H, J=7 Hz).

MS (m/z): 235 ([M+NH$_4$]$^+$).

The above embodiments of the present invention are intended to be illustrative and not restrictive, the scope of the invention being instead defined by the appended claims and equivalencies embraced thereby. It is expected that the particulars of the foregoing description may be readily modified by those skilled in the art without departing from the spirit or essential characteristics thereof.

We claim:

1. A method for preparing a compound having the formula:

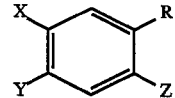

wherein X is chloro or fluoro; one of Y and Z is chloro and the other is nitro; and R is a radical selected from the group consisting of —CCl$_3$, —CH$_2$NO$_2$, —CH(NO$_2$)R$^1$, —CH(CO$_2$R$^1$)$_2$, —CH(C(O)R$^2$)$_2$, —CH(CN)CO$_2$R$^1$, —CH(CO$_2$R$^1$)COR$^2$ and —COR$^2$ where R$^1$ is alkyl or arylalkyl and R$^2$ is alkyl, aryl or arylalkyl and, where appearing more than once in such a radical, R$^1$ and R$^2$ may be the same or different at each occurrence, comprising reacting a nitrobenzene having the formula:

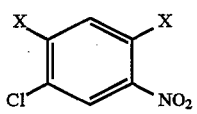

with an appropriate carbanion generated by reacting a base with a nucleophile selected from the group consisting of chloroform, nitroalkanes, enamines, malonates, beta-ketoesters, cyanoacetates, malononitriles and beta-diketones.

2. The method according to claim 1 wherein said carbanion is generated by reacting a base with a nucleophile selected from the group consisting of nitroalkanes of formula $CH(R^{19})(R^{20})NO_2$, enamines of formula $C(NR^{16}R^{17})(R^{14})=CHR^{15}$, malonates of formula $CH(R^{13})(CO_2R^{18})_2$, beta-ketoesters of formula $R^{11}C(O)CH(R^{13})CO_2R^8$, cyanoacetates of formula $CH(CN)(R^{14})CO_2R^{15}$, malononitriles of formula $CH(R^{10})(CN)_2$, and beta-diketones of formula $R^{11}C(O)CH(R^{10})C(O)R^{12}$, where $R^{19}$ and $R^{20}$ are independently selected from the group consisting of hydrogen, alkyl and aryl; $R^{14}$ and $R^{15}$ are independently selected from the group consisting of hydrogen, alkyl and arylalkyl; $R^{16}$ and $R^{17}$ are independently alkyl; $R^{13}$ and $R^{18}$ are independently selected from the group consisting of hydrogen, alkyl and arylalkyl; $R^{11}$ and $R^{12}$ are independently selected from the group consisting of alkyl, aryl and arylalkyl; $R^{10}$ is selected from the group consisting of hydrogen, alkyl, aryl and arylalkyl; and $R^8$ is selected from the group consisting of alkyl of from two to ten carbons and arylalkyl having an alkyl component of from two to ten carbons.

3. The method according to claim 1 wherein said base is selected from the group consisting of amines, amidines, hydroxides, alkoxides, hydrides, carbonates and bicarbonates.

4. The method according to claim 3 wherein said base is DBU or 1,1,3,3-tetramethylguanidine; R is —$CH_2NO_2$ or —$CH(NO_2)CH_3$; X is fluoro; Y is nitro; and Z is chloro.

* * * * *